United States Patent [19]

Lerner

[11] Patent Number: 4,633,009

[45] Date of Patent: Dec. 30, 1986

[54] SYNTHESIS OF METHYL N-METHYLANTHRANILATE

[75] Inventor: David I. Lerner, Teaneck, N.J.

[73] Assignee: Frizsche Dodge & Olcott Inc., New York, N.Y.

[21] Appl. No.: 745,894

[22] Filed: Jun. 18, 1985

[51] Int. Cl.[4] .......................................... C07C 101/54
[52] U.S. Cl. ..................................................... 560/19
[58] Field of Search ......................................... 560/19

[56] References Cited

U.S. PATENT DOCUMENTS 4,002,664  1/1977  Seeger et al. ........................ 560/19

FOREIGN PATENT DOCUMENTS 0160877  9/1942  Austria ................................. 560/19
0716668  1/1942  Fed. Rep. of Germany ........ 560/19

Primary Examiner—Bernard Helfin
Attorney, Agent, or Firm—Cooper, Dunham, Griffin & Moran

[57] ABSTRACT

Methyl N-methylanthranilate is prepared by reductive alkylation of methylanthranilate with formaldehyde and hydrogen in the presence of a hydrogenation catalyst and an acid catalyst.

2 Claims, No Drawings

SYNTHESIS OF METHYL N-METHYLANTHRANILATE

FIELD OF THE INVENTION

This invention relates to the manufacture of methyl N-methylanthranilate.

DESCRIPTION OF THE PRIOR ART

Methyl N-methylanthranilate is of importance to both the flavor and fragrance industries. It is used widely in flavor compositions, such as grape, "Tutti-frutti", and citrus blends. It also finds extensive use in perfumery, particularly in soap and detergent, shampoo, and various cosmetic perfumes.

Various synthetic methods are known for the preparation of methyl N-methylanthranilate. One such method comprises reacting anthranilic acid with methyl iodide in the presence of alkali or with methyl sulfate in an acetic acid solution [Houben and Brassert, Ber., 39, 3235 (1906)] and then esterifying the acid in the usual manner [Schimmel and Co., German Pat. No. 122568 (1900)]. Another method involves reacting isatoic anhydride with a strong base and then methylating with dimethyl sulfate or a methyl halide to form N-methyl isatoic anhydride which is then reacted with methanol. [P. Bedoukian, Perfumery and Flavoring Synthetics, 2nd ed., p. 44 (1967)].

It would therefore be a distinct advance in the art if methyl N-methylanthranilate could be made in an efficient, one-step reaction process.

MATERIALS EMPLOYED

Methyl anthranilate, Sherwin Williams Corp.
Formaldehyde (37% soln.), Ruger Chemical Co., Inc.
Ethyl acetate, J. T. Baker Chemical Co.
K-10 ®, acidified montmorillonite clay, Sud-Chemie A.G.
5% Palladium on carbon catalyst, Engelhard Minerals and Chemicals Corporation.
Platinum oxide catalyst, Engelhard Minerals and Chemicals Corporation.
Raney nickel, Davison Specialty Chem. Co.
Hydrogen, Liquid Carbonic Corporation.
Ethanol, U.S. Industrial Chemicals Co.
Glacial acetic acid, J. T. Baker Chemical Co.

SUMMARY OF THE INVENTION

This invention comprises a convenient process of preparing methyl N-methylanthranilate by reductively alkylating methyl anthranilate with formaldehyde and hydrogen in the presence of a hydrogenation and an acid catalyst.

DETAILED DESCRIPTION OF THE INVENTION

Under typical conditions for reductive alkylation of methyl anthranilate with formaldehyde and hydrogen in the presence of a hydrogenation catalyst, a solid precipitate dimethyl N,N'-methylenedianthranilate (a dimer), is formed. This dimer results from the condensation of 1 mole of formaldehyde with 2 moles of methyl anthranilate and has the following structure:

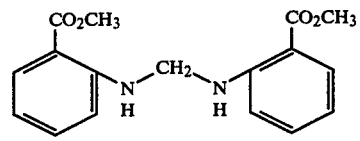

Very minor reductive alkylation, if any, occurs.

It has been unexpectedly found that to efficiently carry out such a reductive alkylation, methyl anthranilate is reacted with formaldehyde or a formaldehyde generating equivalent species in the presence of a hydrogenation and an acid catalyst to produce methyl N-methylanthranilate. Yields greater than 96% of theoretical are obtainable. No dimer was detected when the reductive alkylation was performed according to the inventive process.

In general any acid moiety may be used to catalyze the reductive alkylation. It is preferable to use a weak organic acid rather than a strong inorganic acid. It has been helpful to use solid acidic catalysts such as acidic clays or ion exchange resins which can be separated from the final reaction mixture by filtration. The acid catalyst is preferably used in an amount of between about 0.01 and about 1.0 equivalents (ratio of acid catalyst to substrate), more preferably between about 0.05 to about 0.5 equivalents, most preferably about 0.1 equivalents.

In order to produce good yields of the desired product at least one mole of formaldehyde per mole of methyl anthranilate is employed. In the usual case a minor excess of formaldehyde is employed. Thus the molar ratio of formaldehyde to methyl anthranilate usually ranges from about 0.5 to about 2.0, more preferably from about 0.8 to about 1.2, and most preferably a 1.05 molar ratio is employed.

The hydrogenation catalyst may be chosen from a wide variety of materials including, but not limited to platinum oxide, platinum on carbon, Raney nickel and palladium on carbon. Any hydrogenation catalyst should catalyze the reductive alkylation to varying degrees. One can readily find an acceptable catalyst and catalyst concentration by experimentation. When using 5% platinum on carbon and 5% palladium on carbon the ratio of catalyst to substrate should be between about 1% and about 15% by weight. Raney nickel and platinum oxide catalysts should be used in a ratio of between about 5% and about 20% by weight and between about 0.5% and about 5% by weight, respectively. The catalysts of preference are Raney nickel and palladium on carbon.

The reaction can be carried out using any solvent generally acceptable for hydrogenation. A list of solvents found to be acceptable, but not intended to be limiting, include ethanol, methanol, water, acetic acid, ethyl acetate, cyclohexane or mixtures thereof. The solvent of preference is ethyl acetate. Enough solvent should be used to allow for adequate mixing throughout the reaction.

Again, the reaction may be effected at atmospheric or superatmospheric hydrogen pressures. Usually the reaction is carried out under a hydrogen pressure varying from about 1 atmosphere to about 15 atmosphere, more preferably from about 3 atmosphere to about 8 atmosphere.

Again, the temperature of the reaction may range rather widely depending upon other variables such as pressure and types of catalyst employed. However, usually, the temperatures of the reaction ranges from about 0° C. to about 150° C. more preferably from about 25° C. to about 100° C., and most preferably from about 25° C. to about 75° C.

Again, the reaction time may range rather widely depending upon other variables such as pressure, type of catalyst employed and temperatures. The reaction is run until hydrogen consumption has ceased. Generally, the reaction consumes about 1 mole equivalent of hydrogen.

In one embodiment of the inventive process the reaction is preferably carried out by adding the solvent, methyl anthranilate, formaldehyde, solid acid catalyst, and hydrogenation catalyst to the reaction vessel under agitation. It is preferred that this mixture is maintained at a low temperature (about 0° C.) until the reaction vessel is pressurized with hydrogen. Upon hydrogen pressurization the temperature of the reaction mixture is elevated to the predetermined reaction temperature and reacted until the hydrogen uptake ceases. The reaction mixture is then filtered to remove the solid acid and hydrogenation catalysts and stripped to remove solvent.

By employing this process the synthesis of methyl N-methyl anthranilate is carried out in a simple one-step technique. Moreover, there is no neutralization required with concomitant salt removal and disposal problems. Any corrosion problem involved in using strong acids such as hydrochloric acid may be eliminated. The catalysts themselves can be removed and reused by merely filtering the reaction mixture. Lastly, the corrosive nature of the reaction can be significantly reduced, eliminating the need for expensive corrosion resistant equipment, thereby improving the overall process economics.

The following examples typically illustrate the process of the invention. It is understood, of course, that these examples are given by way of illustration and not as a limitation upon the scope of the invention.

EXAMPLE 1

In a 250 mL Parr shaking glass pressure reactor was placed methyl anthranilate (15.1 g, 0.10 mol), ethyl acetate (70 mL) and 5% palladium on carbon catalyst (1.5 g). To this cooled mixture at 5° C. was added 37% aqueous formaldehyde solution (8 mL, 0.10 mol). The resultant mixture was immediately hydrogenated at room temperature at an initial hydrogen pressure of 50 psig with continuous shaking overnight. Very little hydrogen uptake was observed. After hydrogen uptake had ceased, the mixture was filtered through filter-aid. The filtrate was dried and the solvent was evaporated at reduced pressure. NMR results indicate that most of the methyl anthranilate was converted to the dimer with very minimal conversion to methyl N-methylanthranilate.

EXAMPLE 2

In a 250 mL Parr shaking glass pressure reactor was placed methyl anthranilate (37.75 g, 0.25 mol), 95% ethanol (80 mL), and platinum oxide (0.5 g). To this cooled mixture at 5° C. was added 37% formaldehyde solution (20 mL, 0.25 mol). This resultant mixture was immediately hydrogenated at room temperature at a hydrogen pressure of 50 psig. Over a period of 5 hours no hydrogen uptake was observed. The dimer, however, did form as evidenced by a solid precipitate, but no methyl N-methylanthranilate was produced.

EXAMPLE 3

In a 2L Parr pressure reactor was placed methyl anthranilate (302 g, 2.0 mol), ethyl acetate (700 mL), glacial acetic acid (120 g, 2.0 mol), and 5% palladium on carbon catalyst (30 g). The mixture was cooled to 5° C. and 37% aqueous formaldehyde solution (160 mL, 2.12 mol) was added. The mixture was then hydrogenated at 25° C. at an initial hydrogen pressure of 50 psig with continuous stirring. After hydrogen uptake had ceased (12 h), the mixture was filtered through filter-aid. The filtrate was washed to neutrality with saturated NaHCO$_3$ (3×300 mL) and the layers were separated. The organic layer was washed with saturated NaCl (400 mL), and dried. The solvent was evaporated at reduced pressure. The residue was distilled through a Vigreaux column (30×2 cm) to provide methyl N-methylanthranilate, b$_{12.0}$ 130°-132° C. as a colorless liquid. Yield: 300 g (91% of theor.). GLC purity: 97.3%.

EXAMPLE 4

In a 2 L Parr pressure reactor was placed methyl anthranilate (302 g, 2.0 mol), ethyl acetate (700 mL), K-10 powder (30 g) and 5% palladium on carbon catalyst (30 g). The mixture was cooled to 5° C. and 37% aqueous formaldehyde solution (160 mL, 2.12 mol) was added. The mixture was then hydrogenated at room temperature at an initial hydrogen pressure of 50 psig with continuous stirring. After hydrogen uptake had ceased (7 h), the mixture was filtered through filter-aid. The filtrate was dried and the solvent was evaporated at reduced pressure. The residue was distilled through a Vigreaux column (30×2 cm) to provide methyl N-methylanthranilate, b$_{12.0}$ 130°-132° C. as a colorless liquid. Yield: 317 g (96% of theor.). GLC purity: 99.7%.

EXAMPLE 5

In a 5 gallon Star autoclave was placed methyl anthranilate (6.65 lbs, 20 mol), ethyl acetate (7000 mL) and K-10 powder (300 g). The mixture was cooled to 5° C. Then a 37% aqueous formaldehyde solution (1,600 mL, 21.2 mol) and 5% palladium on carbon catalyst (300 g) were added. The mixture was then hydrogenated at room temperature for 20 hours at an initial hydrogen pressure of 150 psi with continuous stirring. The mixture was filtered, and the solvent was evaporated at reduced pressure. The residue was distilled through a packed column (24×2") to provide methyl N-methylanthranilate b$_{2.0}$ 110° C. as a colorless liquid. Yield: 7.02 lbs (96.5% of theor.). GLC purity: 99%.

EXAMPLE 6

In a 250 mL Parr shaking glass pressure reactor was placed methyl anthranilate (15.1 g, 0.10 mol), ethanol (70 mL), glacial acetic acid (6 g, 0.1 mol) and Raney nickel catalyst (2.1 g). To this cooled mixture at 5° C. was added 37% formaldehyde solution (8 mL, 0.10 mol). The mixture was then hydrogenated at 25° C. at an initial hydrogen pressure of 50 psig with continuous stirring. After hydrogen uptake had ceased (6 h), the mixture was filtered through filter-aid. The filtrate was washed to neutrality with saturated NaHCO$_3$ (2×100 mL), and the layers were separated. The organic layer was washed with saturated NaCl (100 mL) and dried. The solvent was evaporated at reduced pressure. The residue was distilled to provide methyl N-methylanthranilate, b$_{12.0}$ 130°-133° C. as a colorless liquid. Yield: 14 g (85% of theor.). GLC purity: 98.5%.

As will be apparent to those skilled in the art, in the light of the foregoing disclosure, many alterations, modifications, substitutions and combinations are possible in the practice of this invention without departing from the spirit or scope thereof.

What is claimed is:

1. A process for the production of methyl N-methylanthranilate which comprises the reductive alkylation of methyl anthranilate with formaldehyde and hydrogen in the presence of a hydrogenation and a solid acid catalyst, the reductive alkylation reaction being carried out at a temperature in the range from about 0° C. to about 150° C. and under superatmospheric hydrogen pressure in a range from about 1 atmosphere to about 15 atmospheres.

2. A process for the production of methyl anthranilate which comprises the reductive alkylation of methyl anthranilate with formaldehyde and hydrogen in the presence of a hydrogenation and an acidic clay catalyst, the reductive alkylation operation being carried out at a temperature in a range from about 0° C. to about 150° C. under superatmospheric hydrogen pressure in the range from about 1 atmosphere to about 15 atmospheres.

* * * * *